United States Patent [19]

Shinohara et al.

[11] Patent Number: 5,167,709

[45] Date of Patent: Dec. 1, 1992

[54] PIGMENT CONSISTING OF POLYVALENT METAL SALT OF ACYLATED AMINO ACID OR AMIDOSULFONIC ACID AND COSMETIC COMPOSITION CONTAINING THE SAME

[75] Inventors: Ryutaro Shinohara; Toshio Nozaki, both of Chiba; Osamu Tachizawa, Wakayama, all of Japan

[73] Assignee: Kao Corporation, Tokyo, Japan

[21] Appl. No.: 683,153

[22] Filed: Apr. 10, 1991

[30] Foreign Application Priority Data

Apr. 11, 1990 [JP] Japan .................................. 2-95328
Apr. 24, 1990 [JP] Japan .................................. 2-108233

[51] Int. Cl.$^5$ .............................................. C08K 9/04
[52] U.S. Cl. ...................................... 106/504; 106/400; 106/401; 106/419; 106/436; 106/450; 106/456; 106/461; 106/499; 106/503
[58] Field of Search ............... 106/400, 401, 419, 436, 106/450, 456, 461, 499, 504, 503

[56] References Cited

U.S. PATENT DOCUMENTS 2,198,806 8/1938 Epstein et al. .
4,606,914 8/1986 Miyoshi .
4,640,943 2/1987 Meguro et al. ..................... 106/448
4,837,011 6/1989 Macchio et al. .

OTHER PUBLICATIONS

Chemical Abstracts, vol. 110, No. 16, abstract 141226e.
Chemical Abstracts, vol. 112, No. 10, abstracts 83842f.

Primary Examiner—William R. Dixon, Jr.
Assistant Examiner—Scott L. Hertzog
Attorney, Agent, or Firm—Sughrue, Mion, Zinn, Macpeak & Seas

[57] ABSTRACT

A pigment consisting of a polyvalent metal salt of an amidosulfonic acid represented by the following general formula (I):

$$(R^1CO-N(R^2)-X-SO_3)_n M(OH)_{m-n} \quad (I)$$

wherein
$R^1$ represents a straight-chain or branched alkyl, alkenyl or hydroxyalkyl group each having 7 to 21 carbon atoms;
$R^2$ represents a hydrogen atom or a methyl group;
X represents an ethylene group, a propylene group or a $$-CH_2\overset{\overset{\displaystyle OH}{|}}{C}HCH_2- \text{ group;}$$

M represents a polyvalent metal atom;
m represents the valence of M: and
n is an integer of from 1 to 4; and a pigment consisting of a polyvalent metal salt of an acylated amino acid represented by the following general formula (II):

$$[R^1CO-NH-(CH_2)_y-CO_2]_n M(OH)_{m-n} \quad (II)$$

wherein
$R^1$ represents a straight-chain or branched alkyl, alkenyl or hydroxyalkyl group each having 7 to 21 carbon atoms;
y represents a number selected from among 1, 2, 3, 4, 5, 10, and 11;
M represents a polyvalent metal atom;
m represents the valence of M: and
n is an integer of from 1 to 4;

as well as cosmetic compositions containing these pigments are disclosed.

14 Claims, 1 Drawing Sheet

PIGMENT CONSISTING OF POLYVALENT METAL SALT OF ACYLATED AMINO ACID OR AMIDOSULFONIC ACID AND COSMETIC COMPOSITION CONTAINING THE SAME

FIELD OF THE INVENTION

This invention relates to a pigment comprising a polyvalent metal salt of an amidosulfonic acid or an acylated amino acid and an excellent cosmetic composition which contains the pigment, which cosmetic has good spreadability on the skin, high adhesiveness, high smoothness, a good finish, a long makeup life, good molding characteristics and a good feel upon use.

BACKGROUND OF THE INVENTION

Known powdery pigments for cosmetics which are insoluble in water or oil include inorganic extender pigments such as talc and mica; inorganic color pigments such as titanium dioxide and zinc oxide; organic color pigments such as organic tar coloring materials; composite pigments such as mica/titanium; resin powders such as nylon powder; and coated powders prepared by treating the surface of these pigments with a known coating agent such as silicone.

Although these known pigments are employed in cosmetics in an appropriate amount by taking the spreadability, adhesiveness, covering characteristics and molding characteristics thereof into consideration, cosmetics containing them are not always satisfactory in, for example, spreadability, smoothness, adhesiveness, finishing, makeup life, stability and molding characteristics. In the case of a powdery cosmetic containing a common extender pigment such as talc or mica as a base, for example, the use of talc or mica of a large particle size, which are selected in order to enhance smoothness, would make the cosmetic product coarse and, as result, the obtained cosmetic would be poor in, for example, adhesiveness, molding characteristics and makeup life. Sometimes a spherical resin powder such as nylon powder or polystyrene powder has been used. However, such a pigment, which gives a dry feel and has a poor adhesiveness, fails to impart any softness or moist feel to a cosmetic. Further, such powders deteriorate not only the adhesiveness of the cosmetic to the skin but also the molding characteristics thereof.

On the other hand, it has been attempted to add a metal soap to a cosmetic in order to improve the adhesiveness, molding characteristics and makeup life of the cosmetic. However, a metal soap cannot impart satisfactory characteristics including smoothness and adhesiveness to a cosmetic.

Therefore, the art is in need of a pigment which can provide high spreadability, high smoothness, high adhesiveness, long makeup life, high stability and excellent molding characteristics as well as a cosmetic composition which contains such a pigment and has a good feel upon use.

SUMMARY OF THE INVENTION

In light of the above, the present inventor have conducted extensive studies, and, as a result, they found that a cosmetic composition containing a pigment comprising a polyvalent metal salt of an amidosulfonic acid or an acylated amino acid respectively represented by the following general formula (I) and (II) have excellent properties including spreadability, smoothness and a good feel upon use, to thereby reach the present invention.

Accordingly, the present invention provides a pigment consisting of a polyvalent metal salt of an amidosulfonic acid represented by the following general formula (I):

$$(R^1CO-N(R^2)-X-SO_3)_nM(OH)_{m-n} \quad (I)$$

wherein $R^1$ represents a straight-chain or branched alkyl, alkenyl or hydroxyalkyl group each having 7 to 21 carbon atoms;

$R^2$ represents a hydrogen atom or a methyl group;

X represents an ethylene group, a propylene group or a

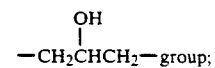

$$-CH_2CH(OH)CH_2-\text{ group};$$

M represents a polyvalent metal atom;

m represents the valence of M; and n is an integer of from 1 to 4;

and a cosmetic composition containing such pigment.

The present invention further provides a pigment consisting of a polyvalent metal salt of an acylated amino acid represented by the following general formula (II):

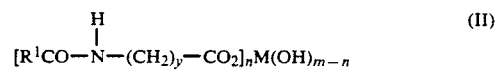

$$[R^1CO-N(H)-(CH_2)_y-CO_2]_nM(OH)_{m-n} \quad (II)$$

wherein $R^1$ represents a straight-chain or branched alkyl, alkenyl or hydroxyalkyl group each having 7 to 21 carbon atoms; y represents a number selected from among 1, 2, 3, 4, 5, 10 and 11;

M represents a polyvalent metal m represents the valence of M: and n is an integer of from 1 to 4;

and a cosmetic composition containing such pigment.

DETAILED DESCRIPTION OF THE INVENTION

Figure 1:
FIG. 1 is a scanning electron microscopic photograph showing the crystal structure of N-lauroyltaurine calcium salt obtained in Production Example 1.

As the group $R^1$ given in the general formulae (I) or (II), examples of the alkyl group include heptyl, octyl, nonyl, decyl, undecyl, dodecyl, tridecyl, tetradecyl, pentadecyl, hexadecyl, heptadecyl, octadecyl, nonadecyl, elcosyl and henicosyl groups; examples of the alkenyl group include 2-heptenyl, 2-octen-8-ynyl, 3,4-dipropyl-1,3-hexadien-5-ynyl, 5,5-dimethyl-1-hexyl, 4-vinyl-1-hepten-5-ynyl, 5-(3-pentenyl)-3,6,8-decatrien-1-ynyl, 6-(1,3-pentadienyl)-2,4,7-dodecatrien-9-ynyl and 2-nonyl-2-butenyl groups; and examples of the hydroxyalkyl group include hydroxyheptyl, hydroxydecyl, hydroxytetradecyl and hydroxynonadecyl groups.

Among them, straight-chain alkyl groups having 9 to 15 carbon atoms are preferred and nonyl, undecyl, tridecyl and pentadecyl groups are more preferred. Examples of the polyvalent metal represented by M include Al, Ca, Zn, Zr, Mg, Fe, Ba and Ti. Among the polyvalent metals, Ca, Zn, Mg and Ba are preferred.

Specific and preferred examples of polyvalent metal salt of the amidosulfonic acid of formula (I) and the acylated amino acid of formula (II) include, for example, N-lauroyltaurine Ca salt, N-lauroyltaurine Ba salt, N-lauroyltaurine Zn salt, N-palmitoyltaurine Ca salt, N-palmitoyltaurine Ba salt, N-lauroyltaurine Zn salt, N-lauroyl-β-alanine Ca salt, N-lauroyl-β-alanine Ba salt, N-lauroyl-β-alanine Zn salt, N-palmitoyl-β-alanine Ca salt, N-palmitoyl-β-alanine Ba salt and, N-palmitoyl-β-alanine Zn salt.

The polyvalent metal salt of an amidosulfonic acid (I), which is used as a pigment component of a cosmetic composition herein should be either insoluble or substantially insoluble in water.

The polyvalent metal salt of an amidosulfonic acid (I) of the present invention may be produced by, for example, a method similar to those employed for synthesizing common metal soaps. That is to say, the pigment of the present invention comprising the polyvalent metal salt of an amidosulfonic acid may be produced by, for example, dissolving a water soluble salt (e.g., Na salt, K salt, $NH_4$ salt, alkanolamine salts) of an amidosulfonic acid represented by the formula:

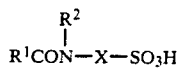

wherein $R^1$, $R^2$ and X are as defined above, in water, adding an aqueous solution of a water soluble polyvalent metal salt in a substantially equivalent amount thereto, preferably within a period of time of from 15 to 120 minutes, salt exchanging, thoroughly stirring, filtering, washing with water and then drying.

Examples of the water soluble polyvalent metal salt to be used include aluminum sulfate, aluminum chloride, aluminum nitrate, aluminum potassium sulfate, magnesium chloride, magnesium sulfate, magnesium nitrate, magnesium potassium sulfate, calcium chloride, zinc chloride, zinc nitrate, zinc sulfate, zinc acetate, zirconium sulfate, zirconium chloride, titanium oxysulfate and titanium tetrachloride.

The particle size of the obtained polyvalent metal salt of an amidosulfonic acid may be increased as the time of adding the water soluble polyvalent metal salt is increased.

The powdery crystals of the polyvalent metal salt of an amidosulfonic acid thus obtained are in the form of needles, columns or plates, depending on the reaction conditions and the salt employed. Monoclinic plates are particularly preferable since they can give an excellent feel upon use in a cosmetic.

The polyvalent metal salt of an amidosulfonic acid pigment (I) thus obtained may be used in a cosmetic composition as such. Alternately, it may be used for treating some other powders to give hydrophobic powders.

Although the particle size of the polyvalent metal salt of an amidosulfonic acid (I) to be used in the cosmetic composition of the present invention is not particularly restricted, the average particle size preferably ranges from 0.1 to 50 μm. When it is smaller than 0.1 μm, a satisfactory smoothness may not be achieved. When it exceeds 50 μm, on the other hand, a coarse feel may become noticeable. The polyvalent metal salt of an amidosulfonic acid (I) is preferably contained in the cosmetic composition of the present invention in an amount of from 0.1 to 99% by weight based on the total weight of the cosmetic composition. When the content thereof is smaller than 0.1% by weight, the above-described effects may not be fully achieved.

The average particle size used herein means the particle size of 50% cumulative distribution in the cumulative distribution of the volume measured by the laser diffraction method using an SK laser manufactured by Seishin Kigyo K.K.

In addition to the above-mentioned polyvalent metal salt of an amidosulfonic acid (I), the cosmetic composition of the present invention may further contain a cosmetic powder as is commonly employed in the art as well as optional components such as various oils, surfactants, wetting agents, water, alcohols, preservatives, UV absorbers, antioxidants and perfumes, if desired or necessary.

The polyvalent metal salt of an acylated amino acid (II), which is used as a pigment component of a cosmetic composition herein should be either insoluble or substantially insoluble in water.

The polyvalent metal salt of an acylated amino acid (II) of the present invention may be produced by, for example, a method similar to those employed for synthesizing common metal soaps. That is to say, the pigment of the present invention comprising the polyvalent metal salt of an acylated amino acid may be produced by, for example, dissolving a water soluble salt (e.g., Na salt, K salt, NH: salt, alkanolamine salts) of an acylated amino acid represented by the formula:

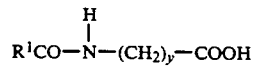

wherein $R^1$ and y are as defined above, in water, adding an aqueous solution of a water soluble polyvalent metal salt thereto, preferably within a period of time of from 15 to 120 minutes, in a substantially equivalent amount, salt exchanging, thoroughly stirring, filtering, washing with water and then drying.

Examples of the water soluble polyvalent metal salt used include aluminum sulfate, aluminum chloride, aluminum nitrate, aluminum potassium sulfate, magnesium chloride, magnesium sulfate, magnesium nitrate, magnesium potassium sulfate, calcium chloride, zinc chloride, zinc nitrate, zinc sulfate, zinc acetate, zirconium sulfate, zirconium chloride, titanium oxysulfate and titanium tetrachloride.

The particle size of the obtained polyvalent metal salt of the acylated amino acid may be increased of as the time of adding the water soluble polyvalent metal salt is increased.

The powdery crystals of the polyvalent metal salt of the acylated amino acid thus obtained are in the form of needles, columns or plates, depending on the reaction conditions and the salt employed. Monoclinic plates are particularly preferable since they can give an excellent feel when used in a cosmetic.

The polyvalent metal salt of the acylated amino acid pigment (II) thus obtained may be used in a cosmetic composition as such. Alternately, it may be used for treating some other powders to give hydrophobic powders.

Although the particle size of the polyvalent metal salt of an acylated amino acid (II) used in the cosmetic composition of the present invention is not particularly restricted, the average particle size preferably ranges from 0.1 to 50 μm. When it is smaller than 0.1 μm, satisfactory smoothness may not be achieved. When it exceeds 50 μm, on the other hand, a coarse feel may become noticeable. The polyvalent metal salt of an acylated amino acid (II) is preferably contained in the cosmetic composition of the present invention in an amount of from 0.1 to 99% by weight based on the total weight of the cosmetic composition. When the content thereof is smaller than 0.1% by weight, the above-described effects cannot be fully achieved.

The average particle size used herein means the particle size of 50% cumulative distribution in the cumulative distribution of the volume measured by the laser diffraction method using an SK laser manufactured by Seishin Kigyo K.K.

In addition to the above-mentioned polyvalent metal salt of an acylated amino acid (II), the cosmetic composition of the present invention may further contain a cosmetic powder as is commonly employed in the art as well as optional components such as various oils, surfactants, wetting agents, water, alcohols, preservatives, UV absorbers, antioxidants and perfumes, if desired or necessary.

Any known cosmetic powder may be used so long as the effects of the present invention are not deteriorated thereby. Examples thereof include inorganic extender pigments such as talc, kaolin, mica, sericite and synthetic mica; inorganic colorants such as titanium oxide, zinc oxide, ultramarine chromium oxide and iron oxide; organic colorants such as organic tar coloring materials and lakes; composite cosmetics such as mica/titanium and iron oxide-coated mica; spherical powders such as nylon powder, polymethyl methacrylate (PMMA) and silica beads; and powders prepared by treating the surface of the above-mentioned cosmetic powders with a coating agent such as a silicone, higher fatty acid, higher alcohol, ester or wax. Either one of these materials or a mixture thereof may be used. When a makeup cosmetic or a body cosmetic is to be produced, it is preferable to select an inorganic powder (for example, talc, kaolin, sericite, mica, titanium oxide, iron oxide, mica/titanium, iron oxide-coated mica) from among the above-mentioned ones.

With respect to optional components, examples of useful oils include liquid paraffin, vaseline, paraffin wax, polyethylene wax, squalane, ceresin wax, beeswax, carnauba wax, candelilla wax, hardened castor oil, olive oil, lanolin, lanolin alcohol, lanolin fatty acids, higher alcohols, fatty acids, synthetic ester oils obtained from higher alcohols and fatty acids and silicone; examples of useful surfactants include anionic surfactants such as soaps, alkyl sulfates and monoalkyl phosphates and nonionic surfactants such as polyoxyethylene alkyl ethers, polyoxyethylene fatty acid esters, polyoxyethylene sorbitan fatty acid esters, sorbitan fatty acid glycerol fatty acid eaters, polyoxyethylene hardened castor oil and polyoxyethylene sorbitol fatty acid esters; examples of useful wetting agents include sorbitol, glycerol, propylene glycol, isopropylene glycol 1,3-butylene glycol, lactic acid and sodium lactate polyethylene glycol; examples of useful preservatives include p-oxybenzoic alkyl esters, sodium benzoate, potassium sorbate and phenoxyethanol; examples of useful antioxidants include tocopherol, sesamol, sesamolin and lecithin; and examples of useful UV absorbers include 2,4-dihydroxybenzophenone and 2,2'-dihydroxy-4-methoxybenzophenone; though the present invention is not restricted thereto.

The form of the cosmetic composition of the present invention is not particularly restricted. Namely, components including those described above may be arbitrarily combined and processed in a conventional manner to thereby give cosmetics of various forms (for example, powders, oils, emulsions, solutions, or aqueous dispersions). More particularly, the cosmetic composition of the present invention may be in the form of, for example, a powder foundation, eye shadow, emulsion foundation, lipstick, cosmetic base, nail enamel, eye-liner, body powder, baby powder or rouge. Among these cosmetics, powder cosmetics comprising from 1 to 80% by weight of the pigment of the present invention, from 1 to 80% by weight of another known cosmetic powder and from 1 to 20% by weight of oils are preferred.

When used in a cosmetic composition, the polyvalent metal salt of an amidosulfonic acid or an acylated amino acid of the present invention gives high smoothness, has roughness, gives high transparency and has good water repellency. When spread onto the skin, it furthermore provides highly excellent effects, namely, giving an appropriate moistening effect without any overcoated feel and showing good water repellency.

Furthermore, the polyvalent metal salt of an amidosulfonic acid or an acylated amino acid of the present invention may be used as particles in a processing lubricant for molding plastics, an extender pigment for paints, a coating lubricant for paper and in recording materials and in a lubricant for plastic processing of metals, by taking advantage of the smoothing effect thereof.

To further illustrate the present invention, the following Production Examples, Examples and Test Example will be given. The present invention is not restricted by these examples but rather is applicable to any makeup cosmetics.

PRODUCTION EXAMPLE 1

20 g of N-lauroyltaurine sodium salt and 380 g of ion exchanged water were introduced into a 1 l four-necked flask provided with a stirrer, a dropping funnel and a thermometer and formulated into a homogeneous solution. The obtained solution was heated to 40° C. under stirring and 135 g of a 5% by weight aqueous solution of calcium chloride was added dropwise thereto from the dropping funnel within 15 minutes while keeping the solution at 40° C. Simultaneously with the addition, crystals of N-lauroyltaurine calcium salt were precipitated. After the completion of the addition, the mixture was further stirred at 40° C. for 1 hour to complete the salt exchange. After the completion of the stirring, the mixture was allowed to stand to cool to room temperature. It was then filtered and washed. The crystals thus obtained were dried at room temperature. Thus, 19.4 g of the target N-lauroyl-taurine calcium salt was obtained as white crystals (yield: 98.9%).

When observed with a scanning electron microscope, the N-lauroyltaurine calcium salt thus obtained was in the form of plates, as shown in FIG. 1.

Analytical data:

|  | Elemental analysis: | |
|---|---|---|
|  | found | calculated |
| Ca (%) | 6.1 | 6.1 |
| N (%) | 4.3 | 4.3 |
| IR (cm$^{-1}$): | | |
| CON | 1655, 1580 | |
| SO$_3$ | 1210 | |

Particle size: Average particle size: 7.9 μm. Determined using an SK LASER MICRON SIZER (manufactured by Seishin Kigyo K.K.), the same will apply hereinafter.

Particle size distribution:

| Particle size (μm) | Cumulative distribution of volume at fixed particle size (%) |
|---|---|
| 1.0 | 1.2 |
| 1.5 | 2.5 |
| 2.0 | 5.9 |
| 3.0 | 12.2 |
| 4.0 | 20.4 |
| 6.0 | 34.5 |
| 8.0 | 50.5 |
| 12.0 | 70.6 |
| 16.0 | 82.2 |
| 24.0 | 95.0 |
| 32.0 | 100.0 |
| 48.0 | 100.0 |
| 64.0 | 100.0 |
| 96.0 | 100.0 |
| 128.0 | 100.0 |
| 192.0 | 100.0 |

PRODUCTION EXAMPLE 2

20 g of N-palmitoyltaurine sodium salt and 380 g of ion exchanged water were introduced into a 1 l four-necked flask provided with a stirrer, a dropping funnel and a thermometer and formulated into a homogeneous solution. The obtained solution was heated to 40° C. under stirring and 115 g of a 5% by weight aqueous solution of calcium chloride was added dropwise thereto from the dropping funnel within 15 minutes. Simultaneously with the addition, crystals of N-palmitoyltaurine calcium salt were precipitated. After the completion of the addition, the mixture was further stirred at 40° C. for 1 hour to complete the salt exchange. After the completion of the stirring, the mixture was allowed to stand to cool to room temperature. Then, it was filtered and washed. The crystals thus obtained were dried at room temperature. Thus, 19.5 g of the target N- palmitoyltaurine calcium salt was obtained as white crystals (yield: 98.3%).

This product was in the form of plates of 2.4 μm in average.

Particle size distribution:

| Particle size (μm) | Cumulative distribution of volume at fixed particle size (%) |
|---|---|
| 1.0 | 9.0 |
| 1.5 | 20.4 |
| 2.0 | 40.4 |
| 3.0 | 66.5 |
| 4.0 | 82.5 |
| 6.0 | 95.3 |
| 8.0 | 100.0 |
| 12.0 | 100.0 |
| 16.0 | 100.0 |
| 24.0 | 100.0 |
| 32.0 | 100.0 |
| 48.0 | 100.0 |
| 64.0 | 100.0 |
| 96.0 | 100.0 |
| 128.0 | 100.0 |
| 192.0 | 100.0 |

PRODUCTION EXAMPLE 3

Similar to the procedure described in Production Examples 1 and 2, a 5% by weight aqueous solution of barium chloride was added dropwise to a homogeneous solution of N-lauroyltaurine sodium salt. Thus, the target compound N-lauroyltaurine barium was obtained as white crystals (yield: 98.7%).

The obtained product was in the form of plates of 3.9 μm in average particle size.

Particle size distribution:

| Particle size (μm) | Cumulative distribution of volume at fixed particle size (%) |
|---|---|
| 1.0 | 7.7 |
| 1.5 | 14.4 |
| 2.0 | 24.5 |
| 3.0 | 39.9 |
| 4.0 | 50.8 |
| 6.0 | 64.0 |
| 8.0 | 74.5 |
| 12.0 | 85.0 |
| 16.0 | 91.4 |
| 24.0 | 98.2 |
| 32.0 | 100.0 |
| 48.0 | 100.0 |
| 64.0 | 100.0 |
| 96.0 | 100.0 |
| 128.0 | 100.0 |
| 192.0 | 100.0 |

PRODUCTION EXAMPLE 4

50 g of N-lauroyl-β-alanine, 7.4 g of sodium hydroxide and 423 g of ion exchanged water were introduced into a 1 l four-necked flask provided with a stirrer, a dropping funnel and a thermometer. The obtained solution was heated to 60° C. under stirring. Then 64.7 g of a 20% by weight aqueous solution of calcium chloride was added dropwise thereto from the dropping funnel within 2 hours while maintaining the solution at 60° C. Simultaneously with the addition, crystals of N-lauroyl-β-alanine calcium salt were precipitated. After the completion of the addition, the mixture was further stirred at 60° C. for 1 hour to complete the salt exchange. After the completion of the stirring, the mixture was allowed to stand to cool to room temperature. It was then filtered and washed. The crystals thus obtained were dried at room temperature. Thus 52.7 g of the target N-lauroyl-β-alanine calcium salt was obtained as white crystals (yield: 98.5%).

Figure 2:
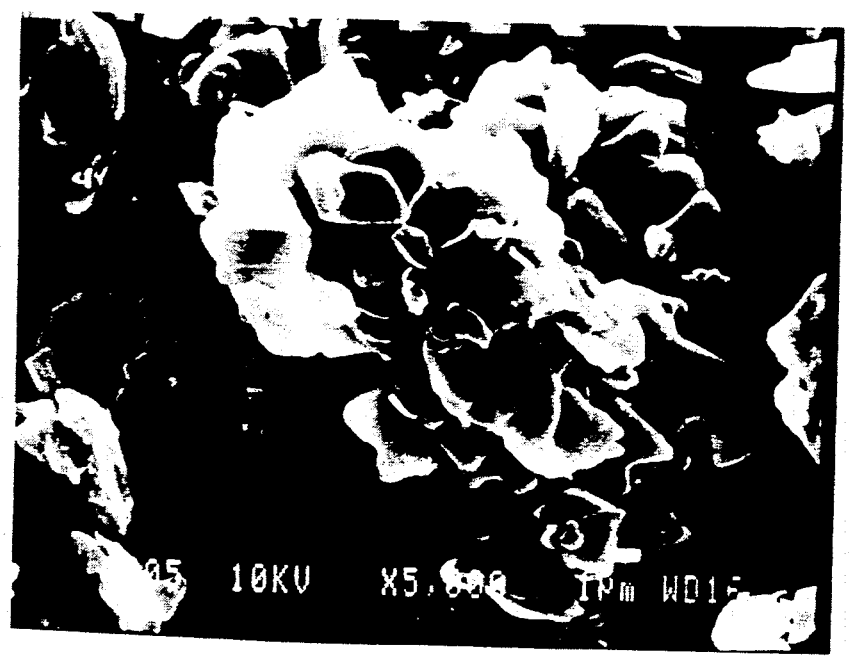
FIG. 2 is a scanning electron microscopic photograph showing the crystal structure of N-lauroyl-β-alanine calcium salt obtained in Production Example 4.

When observed with a scanning electron microscope, the N-lauroyl-β-alanine calcium salt thus obtained was in the form of plates, as shown in FIG. 2.

Analytical data:

| | Elemental analysis: | |
|---|---|---|
| | found | calculated |
| Ca (%) | 6.4 | 6.9 |
| N (%) | 4.15 | 4.8 |

IR (cm$^{-1}$) CON: 1,640, 1545

Particle size: Average particle size: 11.3 μm Determined by using SK LASER MICRON SIZER (manufactured by SEISHIN KIGYO K.K)

Particle size distribution:

| Particle size (μm) | Cumulative distribution of volume at fixed particle size (%) |
|---|---|
| 1.0 | 0.6 |
| 1.5 | 1.3 |
| 2.0 | 3.1 |
| 3.0 | 6.8 |
| 4.0 | 12.0 |
| 6.0 | 21.7 |
| 8.0 | 34.1 |
| 12.0 | 53.1 |
| 16.0 | 68.7 |
| 24.0 | 89.1 |
| 32.0 | 100.0 |
| 48.0 | 100.0 |
| 64.0 | 100.0 |
| 96.0 | 100.0 |
| 128.0 | 100.0 |
| 192.0 | 100.0 |

PRODUCTION EXAMPLE 5

50 g of N-lauroyl-β-alanine, 7.4 g of sodium hydroxide and 410 g of ion exchanged water were introduced into a 1 l four-necked flask provided with a stirrer, a dropping funnel and a thermometer and formulated into a homogeneous solution.

The obtained solution was heated to 60° C. under stirring and 69 g of a 20% by weight aqueous solution of zinc chloride was added dropwise thereto from the dropping funnel within 2 hours. Simultaneously with the addition, crystals of N-lauroyl-β-alanine zinc salt were precipitated. After the completion of the addition, the mixture was further stirred at 60 ° C. for 1 hour to thereby complete the salt exchange. After the completion of the stirring, the mixture was allowed to stand to cool to room temperature. It was then filtered and washed. The crystals thus obtained were dried at room temperature. Thus, 54.8 g of the target N-lauroyl-β-alanine zinc salt was obtained as white crystals (yield: 98.3%).

This product was in the form of plates of 13.9 μm in average.

Particle size distribution

| Particle size (μm) | Cumulative distribution of volume at fixed particle size (%) |
|---|---|
| 1.0 | 0.6 |
| 1.5 | 1.3 |
| 2.0 | 2.8 |
| 3.0 | 5.9 |
| 4.0 | 10.0 |
| 6.0 | 17.4 |
| 8.0 | 27.4 |
| 12.0 | 42.9 |
| 16.0 | 57.5 |
| 24.0 | 79.4 |
| 32.0 | 93.0 |
| 48.0 | 99.3 |
| 64.0 | 99.3 |
| 96.0 | 99.9 |
| 128.0 | 100.0 |
| 192.0 | 100.0 |

PRODUCTION EXAMPLE 6

In a procedure similar to those described in Production Examples 4 and 5, 20 g of N-lauroylaminohexanoic acid, 2.6 g of sodium hydroxide, 180 g of ion exchanged water and 71 g of 10% by weight aqueous solution of calcium chloride were used. Thus, 21.1 g of the target N-lauroylaminohexanoic acid calcium salt was obtained as white crystals (yield: 99.6%).

The obtained product was in the form of plates of 6.7 μm in average particle size.

Particle size distribution:

| Particle size (μm) | Cumulative distribution of volume at fixed particle size (%) |
|---|---|
| 1.0 | 3.6 |
| 1.5 | 6.9 |
| 2.0 | 12.4 |
| 3.0 | 20.9 |
| 4.0 | 29.7 |
| 6.0 | 44.2 |
| 8.0 | 60.1 |
| 12.0 | 78.5 |
| 16.0 | 87.6 |
| 24.0 | 97.2 |
| 32.0 | 100.0 |
| 48.0 | 100.0 |
| 64.0 | 100.0 |
| 96.0 | 100.0 |
| 128.0 | 100.0 |
| 192.0 | 100.0 |

TEST EXAMPLE 1

The relative coefficients of friction of the polyvalent metal N-amidosulfonates produced in Production Examples 1 to 3 and those of mica and sericite, which are extender pigments, were determined in the following manner. A definite amount of each sample was applied onto a tracing paper and the coefficient of friction thereof was measured using a surface properties tester Heidon 14 (manufactured by Shinto Kagaku K.K.). The ratio of the coefficient of friction thus measured to that of the tracing paper per se was referred to as the relative coefficient of friction.

Table 1 shows the results.

TABLE 1

| sample | Relative coefficient of friction |
|---|---|
| Invention product: | |

TABLE 1-continued

| sample | Relative coefficient of friction |
|---|---|
| N-lauroyltaurine Ca salt (Production Example 1) | 0.98 |
| N-palmitoyltaurine Ca salt (Production Example 2) | 0.95 |
| N-lauroyltaurine Ba salt (Production Example 3) | 1.32 |
| Comparative sample: | |
| mica | 3.98 |
| sericite | 4.50 |

These results indicate that the products of the present invention have low coefficients of friction and thus show high spreadability when used in a cosmetic.

TEST EXAMPLE 2

The relative coefficients of friction of the polyvalent metal salts of acylated amino acids produced in Production Examples 4 to 6 and those of mica and sericite, which are extender pigments, were determined in the following manner. A definite amount of each sample was applied onto a tracing paper and the coefficient of friction thereof was measured using a surface properties tester Heidon 14 (manufactured by Shinto Kagaku K.K.). The ratio of the coefficient of friction thus measured to that of the tracing paper per se was referred to as the relative coefficient of friction.

Table 2 shows the results.

TABLE 2

| sample | Relative coefficient of friction |
|---|---|
| Invention product: | |
| N-lauroyl-$\beta$-alanine Ca salt (Production Example 4) | 1.25 |
| N-lauroyl-$\beta$-alanine Zn salt (Production Example 5) | 1.52 |
| N-lauroylaminohexane Ca salt (Production Example 6) | 1.32 |
| Comparative sample: | |
| mica | 3.98 |
| sericite | 4.50 |

These results indicate that the products of the present invention have low coefficients of friction and thus show high spreadability when used in a cosmetic.

EXAMPLE 1

Powder foundation

| | Formulation | (by weight %) |
|---|---|---|
| (1) | N-lauroyltaurine Ca salt (Product Example 1) | 20 |
| (2) | talc | balance |
| (3) | sericite | 10 |
| (4) | titanium oxide | 1 |
| (5) | red iron oxide | 1.5 |
| (6) | black iron oxide | 0.2 |
| (7) | yellow iron oxide | 2 |
| (8) | fine wax powder (pressing aid) | 10 |
| (9) | perfume | 0.1 |
| | Total | 100. |

The following production method was used.

The powdery components were mixed together and ground. Then the mixture was introduced into a Henschel mixer and the oil and the perfume were added thereto. After homogeneously mixing, the mixture was press molded in a metal plate to thereby give the desired product. The foundation thus obtained was excellent in texture including spreadability and had good water repellency and high compatibility with the skin.

EXAMPLE 2

Loose-type face powder

| | Formulation | (% by weight) |
|---|---|---|
| (1) | N-palmitoyltaurine Ca salt (Production Example 2) | 50 |
| (2) | talc | balance |
| (3) | titanium oxide | 0.5 |
| (4) | red iron oxide | 0.1 |
| (5) | liquid paraffin | 1 |
| (6) | perfume | 0.1 |
| | Total | 100. |

The following production method was used.

The powdery components (1) to (4) were mixed together and ground. Then the mixture was introduced into a Henschel mixer and the oil and the perfume were added thereto. After homogeneously mixing, the mixture was passed through a sieve to thereby give the desired product.

The loose-type face powder thus obtained was an excellent product since it showed good spreadability without a powdery feel as observed with conventional loose-type face powders.

EXAMPLE 3

Oily foundation

| | Formulation | (% by weight) |
|---|---|---|
| (1) | N-lauroyltaurine Ba salt (Production Example 3) | 20 |
| (2) | talc | balance |
| (3) | kaolin | 5 |
| (4) | titanium oxide | 5 |
| (5) | red iron oxide | 1 |
| (6) | black iron oxide | 0.1 |
| (7) | yellow iron oxide | 0.6 |
| (8) | squalane | 25 |
| (9) | isopropyl palmitate | 15 |
| (10) | ceresin | 7 |
| (11) | perfume | 0.1 |
| | Total | 100. |

The following production method was used.

The powdery components were mixed together and ground. Then the mixture was added to the oily components, which had been separately heated, under stirring. After homogeneously mixing, the mixture was packed in a metal plate and cooled to thereby give the desired product. The oily type face powder thus obtained was excellent in texture including spreadability and had good water repellency and high compatibility with the skin.

EXAMPLE 4

Creamy foundation

| | Formulation | (% by weight) |
|---|---|---|
| (1) | N-palmitoyltaurine Ca salt (Production Example 2) | 5 |
| (2) | N-lauroyltaurine Ba salt (Production Example 3) | 10 |
| (3) | titanium oxide | 5 |
| (4) | red iron oxide | 1 |
| (5) | black iron oxide | 0.1 |
| (6) | yellow iron oxide | 0.6 |
| (7) | water | balance |
| (8) | preservative | 0.1 |
| (9) | triethanolamine | 1.2 |
| (10) | sorbitol | 3 |
| (11) | stearic acid | 5 |
| (12) | lipophilic glycerol monostearate | 2.5 |
| (13) | cetostearyl alcohol | 1 |
| (14) | propylene glycol monolaurate | 3 |
| (15) | squalane | 25 |
| (16) | olive oil | 8 |
| (17) | perfume | 0.1 |
| | Total | 100. |

The following production method was used.

Powdery components (1) to (6) were mixed together and ground. Separately, a solution comprising the aqueous phase components (7) to (10) was prepared and the ground powdery components were dispersed therein followed by heating to 75° C. Then the oily components (11) to (16) molten by heating to 80° C. were added to the aqueous phase prepared above under stirring and emulsified therein. The obtained emulsion was cooled under stirring and perfume (17) was added thereto at 50° C. The mixture was then cooled under stirring to yield the desired product.

EXAMPLE 5

Finishing powder

| | Formulation | (% by weight) |
|---|---|---|
| (1) | mica | balance |
| (2) | N-lauroyltaurine Ca salt (Production Example 1) | 50 |
| (3) | talc | 20 |
| (4) | titanium oxide | 0.5 |
| (5) | red iron oxide | 0.1 |
| (6) | yellow iron oxide | 0.1 |
| (7) | black iron oxide | 0.01 |
| (8) | liquid paraffin | 8 |
| (9) | beeswax | 2 |
| (10) | preservative | trace |
| (11) | perfume | trace |
| | Total | 100. |

The following production method was used.

Components (1) to (7) were mixed together and ground. Then the mixture was introduced into a high-speed blender and components (8) to (10) which had been mixed and melted by heating to at 80° C. were added thereto. After homogeneously mixing, component (11) was further added thereto and the obtained mixture was ground again and passed through a sieve. The mixture was then compression-molded in a metal plate to give the desired product.

EXAMPLE 6

Creamy foundation

| | Formulation | (% by weight) |
|---|---|---|
| (1) | stearic acid | 5.5 |
| (2) | lipophilic glycerol monostearate | 2.5 |
| (3) | cetostearyl alcohol | 1 |
| (4) | propylene glycol monolaurate | 3 |
| (5) | squalane | 7 |
| (6) | olive oil | 8 |
| (7) | water | balance |
| (8) | preservative | trace |
| (9) | triethanolamine | 1.2 |
| (10) | sorbitol | 3 |
| (11) | titanium oxide | 10 |
| (12) | talc | 5 |
| (13) | color pigment | trace |
| (14) | N-palmitoyltaurine Ca salt (Production Example 2) | 8 |
| (15) | perfume | trace |
| | Total | 100. |

The following production method was used.

Compound (11) to (14) were mixed together and ground. Separately. The aqueous phase components (7) to (10) were mixed together to thereby give a solution in which ground components (11) to (14) were dispersed followed by heating to 75° C. The oily phase components (1) to (6) were melted by heating to 80° C. and would then added to the aqueous phase prepared above under stirring and emulsified therein. The obtained emulsion was cooled under stirring and then perfume (15) was added thereto at 50° C. The mixture was cooled under stirring to thereby give the desired product.

EXAMPLE 7

O/W type cream

| | Formulation | (% by weight) |
|---|---|---|
| (1) | beeswax | 5.5 |
| (2) | cetanol | 4.5 |
| (3) | hydrogenated lanolin | 7 |
| (4) | squalane | 33 |
| (5) | fatty acid glycerol | 3.5 |
| (6) | lipophilic glycerol monostearate | 2 |
| (7) | polyoxyethylene sorbitan monolaurate (20 E.O.) | 2 |
| (8) | N-lauroyltaurine Ba salt (Production Example 3) | 8 |
| (9) | perfume | trace |
| (10) | preservative | trace |
| (11) | antioxidant | trace |
| (12) | propylene glycol | 5 |
| (13) | water | trace |
| | Total | 100. |

The following production method was used.

An aqueous phase comprising components (8), (10), (12) and (13) was mixed under stirring and maintained at 80° C. The other components were mixed together and melted by heating followed by maintaining those components at 80° C. To the oily phase thus obtained was added the above-mentioned aqueous phase followed by preliminarily emulsifying. After homogeneously emulsifying in a homomixer, the mixture was cooled to 30° C. to thereby give the desired product.

EXAMPLE 8

Solid face powder

| | Formulation | (% by weight) |
|---|---|---|
| (1) | mica | balance |
| (2) | N-lauroyltaurine Ca salt (Production Example 1) | 50 |
| (3) | talc | 20 |
| (4) | titanium oxide | 0.5 |
| (5) | red iron oxide | 0.1 |
| (6) | yellow iron oxide | 0.1 |
| (7) | black iron oxide | 0.01 |
| (8) | liquid paraffin | 8 |
| (9) | beeswax | 2 |
| (10) | preservative | trace |
| (11) | perfume | trace |
| | Total | 100. |

The following production method was used.

Components (1) to (7) were mixed together and ground. Then the ground mixture was introduced into a high-speed blender. The components (8) to (10), which had been mixed and melted at 80° C., were added thereto followed by homogenously mixing. The component (11) was added to the obtained mixture. The resulting mixture was ground again, passed through a sieve and compression-molded in a metal plate to give the desired product.

EXAMPLE 9

Rouge

| | Formulation | (% by weight) |
|---|---|---|
| (1) | mica | balance |
| (2) | N-palmitoyltaurine Ca salt (Production Example 2) | 50 |
| (3) | talc | 20 |
| (4) | titanium oxide | 4 |
| (5) | zinc stearate | 5 |
| (6) | rice starch | 5 |
| (7) | coloring material | 3 |
| (8) | liquid paraffin | 3 |
| (9) | preservative | trace |
| (10) | perfume | trace |
| | Total | 100. |

The following production method was used.

Components (1) to (7) were mixed together and color developed. Then, components (8) to (10) were added thereto by spraying in a mixer. After homogeneously mixing, the obtained mixture was passed through a sieve and compressed in a metal plate with a press to give the desired product.

EXAMPLE 10

Eye shadow

| | Formulation | (% by weight) |
|---|---|---|
| (1) | mica | balance |
| (2) | N-lauroyltaurine Ba salt (Production Example 3) | 50 |
| (3) | talc | 5 |
| (4) | mica/titanium | 5 |
| (5) | zinc stearate | 5 |
| (6) | zinc laurate | 3 |
| (7) | color pigment | 10 |
| (8) | liquid paraffin | 7.5 |
| (9) | preservative | trace |
| (10) | perfume | trace |
| | Total | 100. |

The following production method was used.

Components (1) to (7) were mixed together and color developed. Then, components (8) to (10) were added thereto by spraying in a mixer. After homogeneously mixing, the mixture was passed through a sieve and compressed in a metal plate with a press to give the desired product.

EXAMPLE 11

Lipstick

| | Formulation | (% by weight) |
|---|---|---|
| (1) | titanium oxide | 1 |
| (2) | Red No. 201 | 1 |
| (3) | Red No. 202 | 2 |
| (4) | Yellow No. 4 aluminum lake | 1 |
| (5) | Red No. 223 | 0.1 |
| (6) | N-lauroyltaurine Ca salt (Production Example 1) | 5 |
| (7) | castor oil | balance |
| (8) | octyl dodecanol | 15 |
| (9) | lanolin | 5 |
| (10) | liquid lanolin | 5 |
| (11) | beeswax | 5 |
| (12) | ozokerite | 4 |
| (13) | candelilla wax | 7 |
| (14) | carnauba wax | 1 |
| (15) | antioxidant | trace |
| (16) | preservative | trace |
| (17) | perfume | trace |
| | Total | 100. |

The following production method was used.

Components (7) to (14) were melted by heating and homogeneously mixed together. Then, components (1) to (6) were added thereto and the system was homogeneously dispersed by kneading in a roll mill. Next, the dispersion was melted again and components (15) to (17) were added thereto. After defoaming, the mixture was poured into a mold and cooled quickly to mold it. Then, it was taken out and packed in a container. After formulating into a stick, it was passed through a flame to thereby give it a uniform surface.

EXAMPLE 12

Eye liner

| | Formulation | (% by weight) |
|---|---|---|
| (1) | carnauba wax | 5 |
| (2) | beeswax | 1 |
| (3) | microcrystalline wax | 10 |
| (4) | white vaseline | 1 |
| (5) | light liquid isoparaffin | balance |
| (6) | organic bentonite | 0.5 |
| (7) | N-lauroyltaurine Ba salt (Production Example 3) | 10 |
| (8) | titanium oxide | 3 |
| (9) | carbon black | 2 |
| (10) | preservative | trace |
| | Total | 100. |

The following production method was used.

Component (6) was added to a portion of component (5) and the obtained mixture was dispersed through a colloid mill to thereby give a gel. On the other hand, components (1) to (4) and (10) were mixed together and dissolved by heating. After adding the components (7) to (9), the mixture was cooled and kneaded in a roll mill. After melting by heating again, the bentonite gel as obtained above and the balance of component (5) were added followed by cooling under stirring to give the desired product.

EXAMPLE 13

Powder foundation

| | Formulation | (% by weight) |
|---|---|---|
| (1) | N-lauroyl-β-alanine Ca salt (Production Example 4) | 20 |
| (2) | talc | balance |
| (3) | sericite | 10 |
| (4) | titanium oxide | 1 |
| (5) | red iron oxide | 1.5 |
| (6) | black iron oxide | 0.2 |
| (7) | yellow iron oxide | 2 |
| (8) | fine wax powder (pressing aid) | 10 |
| (9) | perfume | 0.1 |
| | Total | 100.0 |

The following production method was used.

The powdery components were mixed together and ground. Then the mixture was introduced into a Henschel mixer and the oil and the perfume were added thereto. After homogeneously mixing, the mixture was press-molded in a metal plate to thereby give the desired product. The foundation thus obtained was excellent in texture, including spreadability, and had good water repellency and high compatibility with the skin.

EXAMPLE 14

Loose-type face powder

| | Formulation | (% by weight) |
|---|---|---|
| (1) | N-lauroyl-β-alanine Zn salt (Production Example 5) | 50 |
| (2) | talc | balance |
| (3) | titanium oxide | 0.5 |
| (4) | red iron oxide | 0.1 |
| (5) | liquid paraffin | 1 |
| (6) | perfume | 0.1 |
| | Total | 100. |

The following production method was used.

The powdery components were mixed together and ground. Then the mixture was introduced into a Henschel mixer and the oil and the perfume were added thereto. After homogeneously mixing, the mixture was passed through a sieve to thereby give the desired product.

The loose-type face powder thus obtained was an excellent product since it showed good spreadability without a powdery feel as observed with conventional loose-type face powders.

EXAMPLE 15

Oily foundation

| | Formulation | (% by weight) |
|---|---|---|
| (1) | N-lauroylaminohexanoic acid Ca salt (Production Example 6) | 20 |
| (2) | talc | balance |
| (3) | kaolin | 5 |
| (4) | titanium oxide | 5 |
| (5) | red iron oxide | 1 |
| (6) | black iron oxide | 0.1 |
| (7) | yellow iron oxide | 0.6 |
| (8) | squalane | 25 |
| (9) | isopropyl palmitate | 15 |
| (10) | ceresin | 7 |
| (11) | perfume | 0.1 |
| | Total | 100. |

The following production method was used.

The powdery components were mixed together and ground. Then the mixture was added to the oily components, which had been separately heated to melt, under stirring. After homogeneously mixing, the mixture was packed in a metal plate and cooled to thereby give the desired product. The oily type face powder thus obtained was excellent in texture, including spreadability, and had good water repellency and high compatibility with the skin.

EXAMPLE 16

Creamy foundation

| | Formulation | (% by weight) |
|---|---|---|
| (1) | N-lauroyl-β-alanine Zn salt (Production Example 5) | 5 |
| (2) | N-lauroylaminohexanoic acid Ca salt (Production Example 6) | 10 |
| (3) | titanium oxide | 5 |
| (4) | red iron oxide | 1 |
| (5) | black iron oxide | 0.1 |
| (6) | yellow iron oxide | 0.6 |
| (7) | water | Balance |
| (8) | preservative | 0.1 |
| (9) | triethanolamine | 1.2 |
| (10) | sorbitol | 3 |
| (11) | stearic acid | 5 |
| (12) | lipophilic glycerol monostearate | 2.5 |
| (13) | cetostearyl alcohol | 1 |
| (14) | propylene glycol monolaurate | 3 |
| (15) | squalane | 25 |
| (16) | olive oil | 8 |
| (17) | perfume | 0.1 |
| | Total | 100.0 |

The following production method was used.

Powdery components (1) to (6) were mixed together and ground. Separately, a solution comprising aqueous phase components (7) to (10) was prepared and the ground powdery components were dispersed therein followed by heating to 75° C. Then, oily components (11) to (16) which had been melted by heating to 80° C. were added to the aqueous phase prepared above under stirring and emulsified therein. The obtained emulsion was cooled under stirring and perfume (17) was added thereto at 50° C. The mixture was then cooled under stirring to give the desired product.

EXAMPLE 17

Finishing powder

| | Formulation | (% by weight) |
|---|---|---|
| (1) | mica | balance |
| (2) | N-lauroyl-β-alanine Ca salt (Production Example 4) | 50 |
| (3) | talc | 20 |
| (4) | titanium oxide | 0.5 |
| (5) | red iron oxide | 0.1 |

-continued

| Formulation | | (% by weight) |
|---|---|---|
| (6) | yellow iron oxide | 0.1 |
| (7) | black iron oxide | 0.01 |
| (8) | liquid paraffin | 8 |
| (9) | beeswax | 2 |
| (10) | preservative | trace |
| (11) | perfume | trace |
| | Total | 100.0 |

The following production method was used.

Components (1) to (7) were mixed together and ground. Then the mixture was introduced into a high-speed blender and components (8) to (10) melted at 80° C. were added thereto. After homogeneously mixing, component (11) was further added thereto and the obtained mixture was ground again and passed through a sieve. The mixture as then compression-molded in a metal plate to give the desired product.

EXAMPLE 18

Creamy foundation

| Formulation | | (% by weight) |
|---|---|---|
| (1) | stearic acid | 5.5 |
| (2) | lipophilic glycerol monostearate | 2.5 |
| (3) | cetostearyl alcohol | 1 |
| (4) | propylene glycol monolaurate | 3 |
| (5) | squalane | 7 |
| (6) | olive oil | 8 |
| (7) | water | balance |
| (8) | preservative | trace |
| (9) | triethanolamine | 1.2 |
| (10) | sorbitol | 3 |
| (11) | titanium oxide | 10 |
| (12) | talc | 5 |
| (13) | color pigment | trace |
| (14) | N-lauroyl-β-alanine Zn salt (Production Example 5) | 8 |
| (15) | perfume | trace |
| | Total | 100.0 |

The following production method was used.

Components (11) to (14) were mixed together and ground. Separately, aqueous phase components (7) to (10) were mixed together to thereby give a solution and then ground components (11) to (14) were dispersed therein followed by heating to 75° C. The oily phase components (1) to (6) were then melted by heating to 80° C. and added to the aqueous phase prepared above under stirring and emulsified therein. The obtained emulsion was cooled under stirring and then perfume (15) was added thereto at 50° C. The mixture was cooled under stirring to thereby give the desired product.

EXAMPLE 19

O/W type cream

| Formulation | | (% by weight) |
|---|---|---|
| (1) | beeswax | 5.5 |
| (2) | cetanol | 4.5 |
| (3) | hydrogenated lanolin | 7 |
| (4) | squalane | 33 |
| (5) | fatty acid glycerol | 3.5 |
| (6) | lipophilic glycerol monostearate | 2 |
| (7) | polyoxyethylene sorbitan monolaurate (20 E.O.) | 2 |
| (8) | N-lauroyaminohexanoic acid Ca salt (Production Example 6) | 8 |

-continued

| Formulation | | (% by weight) |
|---|---|---|
| (9) | perfume | trace |
| (10) | preservative | trace |
| (11) | antioxidant | trace |
| (12) | propylene glycol | 5 |
| (13) | water | trace |
| | Total | 100.0 |

The following production method was used.

An aqueous phase comprising components (8), (10), (12) and (13) was mixed under stirring and maintained at 80° C. The other components were mixed together and melted by heating followed by maintaining the same at 80° C. To the oily phase thus obtained was added the above-mentioned aqueous phase followed by preliminarily emulsifying. After homogeneously emulsifying in homomixer, the mixture was cooled to 30° C. to thereby give the desired product.

EXAMPLE 20

Solid face powder

| Formulation | | (% by weight) |
|---|---|---|
| (1) | mica | balance |
| (2) | N-lauroyl-β-alanine Ca salt (Production Example 4) | 50 |
| (3) | talc | 20 |
| (4) | titanium oxide | 0.5 |
| (5) | red iron oxide | 0.1 |
| (6) | yellow iron oxide | 0.1 |
| (7) | black iron oxide | 0.01 |
| (8) | liquid paraffin | 8 |
| (9) | beeswax | 2 |
| (10) | preservative | trace |
| (11) | perfume | trace |
| | Total | 100.0 |

The following production method was used.

Components (1) to (7) were mixed together and ground. Then the mixture was introduced into a high-speed blender. Components (8) to (10), which had been mixed and melted at 80° C., were added thereto followed by homogeneously mixing. Component (11) was then added to the obtained mixture. The resulting mixture was ground again, passed through a sieve and compression-molded in a metal plate to give the desired product.

EXAMPLE 21

Rouge

| Formulation | | (% by weight) |
|---|---|---|
| (1) | mica | balance |
| (2) | N-lauroyl-β-alanine Zn salt (Production Example 5) | 50 |
| (3) | talc | 20 |
| (4) | titanium oxide | 4 |
| (5) | zinc stearate | 5 |
| (6) | rice starch | 5 |
| (7) | coloring material | 3 |
| (8) | liquid paraffin | 3 |
| (9) | preservative | trace |
| (10) | perfume | trace |
| | Total | 100.0 |

The following production method was used.

Components (1) to (7) were mixed together and color developed. Then, components (8) to (10) were added thereto by spraying in a mixer. After homogeneously mixing, the obtained mixture was passed through a sieve and compressed in a metal plate with a press to give the desired product.

EXAMPLE 22

Eye shadow

| | Formulation | (% by weight) |
|---|---|---|
| (1) | mica | balance |
| (2) | N-lauroylaminoxanoic acid Ca salt (Production Example 6) | 50 |
| (3) | talc | 5 |
| (4) | mica/titanium | 5 |
| (5) | zinc stearate | 5 |
| (6) | zinc laurate | 3 |
| (7) | color pigment | 10 |
| (8) | liquid paraffin | 7.5 |
| (9) | preservative | trace |
| (10) | perfume | trace |
| | Total | 100.0 |

The following production method was used.

Components (1) to (7) were mixed together and color developed. Then, components (8) to (10) were added thereto by spraying in a mixer. After homogeneously mixing, the mixture was passed through a sieve and compressed in a metal plate with a press to give the desired product.

EXAMPLE 23

Lipstick

| | Formulation | (% by weight) |
|---|---|---|
| (1) | titanium oxide | 1 |
| (2) | Red No. 201 | 1 |
| (3) | Red No. 202 | 2 |
| (4) | Yellow No. 4 aluminum lake | 1 |
| (5) | Red No. 223 | 0.1 |
| (6) | N-lauroyl-β-alanine Ca salt (Production Example 4) | 5 |
| (7) | castor oil | balance |
| (8) | octyl dodecanol | 15 |
| (9) | lanolin | 5 |
| (10) | liquid lanolin | 5 |
| (11) | beeswax | 5 |
| (12) | ozokerite | 4 |
| (13) | candelilla wax | 7 |
| (14) | carnauba wax | 1 |
| (15) | antioxidant | trace |
| (16) | preservative | trace |
| (17) | perfume | trace |
| | Total | 100.0 |

The following production method was used.

Components (7) to (14) were melted by heating and homogeneously mixed together. Then, components (1) to (6) were added thereto and the system was homogeneously dispersed by kneading in a roll mill. Next, the dispersion was again melted and components (15) to (17) were added thereto. After defoaming, the mixture was poured into a mold and cooled quickly to mold it. Then, it was released from the mold and packed in a container. After formulating into the same into stick from, it was passed through flame to thereby give it a uniform surface.

EXAMPLE 24

Eye liner

| | Formulation | (% by weight) |
|---|---|---|
| (1) | carnauba wax | 5 |
| (2) | beeswax | 1 |
| (3) | microcrystalline wax | 10 |
| (4) | white vaseline | 1 |
| (5) | light liquid isoparaffin | balance |
| (6) | organic bentonite | 0.5 |
| (7) | N-lauroylaminohexanoic acid Ca salt (Production Example 6) | 10 |
| (8) | titanium oxide | 3 |
| (9) | carbon black | 2 |
| (10) | preservative | trace |
| | Total | 100.0 |

The following production method was used.

Component (6) was added to a portion of component (5) and the obtained mixture was dispersed through a colloid mill to thereby give a gel. On the other hand, components (1) to (4) and (10) were mixed together and dissolved by heating. After adding components (7) to (9) thereto, the mixture was cooled and kneaded in a roll mill. After melting by heating again, the bentonite gel as obtained above and the balance of component (5) were added thereto followed by cooling under stirring to give the desired product.

While the invention has been described in detail and with reference to specific examples thereof, it will be apparent to one skilled in the art that various changes and modifications can be made therein without departing from the spirit and scope thereof.

What is claimed is:

1. A pigment consisting of a polyvalent metal salt of an amidosulfonic acid represented by the following general formula (I):

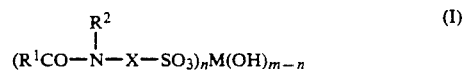

$$(R^1CO-N-X-SO_3)_n M(OH)_{m-n} \quad (I)$$

wherein
R$^1$ represents a straight-chain or branched alkyl, alkenyl or hydroxyalkyl group each having 7 to 21 carbon atoms;
R$^2$ represents a hydrogen atom or a methyl group;
X represents an ethylene group, a propylene group or a

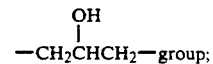

$$-CH_2CHCH_2- \text{ group};$$
(with OH above the central carbon)

M represents a polyvalent metal atom;
m represents the valence of M: and
n is an integer of from 1 to 4.

2. A cosmetic composition containing a pigment of claim 1.

3. A cosmetic composition of claim 2, wherein said pigment is contained in an amount of from 0.1 to 99% by weight.

4. A cosmetic composition containing from 1 to 80% by weight of a pigment of claim 1, from 1 to 80% by weight of another cosmetic powder, and from 1 to 20% by weight of an oil.

5. A pigment consisting of a polyvalent metal salt of an acylated amino acid represented by the following general formula (II):

$$[R^1CO-\underset{|}{\overset{H}{N}}-(CH_2)_y-CO_2]_n M(OH)_{m-n} \quad (II)$$

wherein
- $R^1$ represents a straight-chain or branched alkyl, alkenyl or hydroxyalkyl group each having 7 to 21 carbon atoms; y represents a number selected from among 1, 2, 3, 4, 5, 10, and 11;
- M represents a polyvalent metal atom;
- m represents the valence of M: and
- n is an integer of from 1 to 4.

6. A cosmetic composition containing a pigment of claim 5.

7. A cosmetic composition of claim 6, wherein said pigment is contained in an amount of from 0.1 to 99% by weight.

8. A cosmetic composition containing from 1 to 80% by weight of a pigment of claim 5, from 1 to 80% by weight of another cosmetic powder, and from 1 to 20% by weight of an oil.

9. A method for improving spreadability of a cosmetic composition, which comprises admixing a pigment of claim 1 into the cosmetic composition.

10. A method for improving adhesiveness of a cosmetic composition, which comprises admixing a pigment of claim 1 into the cosmetic composition.

11. A method for improving smoothness of a cosmetic composition, which comprises admixing a pigment of claim 1 into the cosmetic composition.

12. A method for improving spreadability of a cosmetic composition, which comprises admixing a pigment of claim 5 into the cosmetic composition.

13. A method for improving adhesiveness of a cosmetic composition, which comprises admixing a pigment of claim 5 into the cosmetic composition.

14. A method for improving smoothness of a cosmetic composition, which comprises admixing a pigment of claim 5 into the cosmetic composition.

* * * * *